US012754182B2

(12) United States Patent
Russell et al.

(10) Patent No.: US 12,754,182 B2
(45) Date of Patent: Oct. 6, 2026

(54) IFNβ AS A PHARMACODYNAMIC MARKER IN VSV-IFNβ-NIS ONCOLYTIC THERAPY

(71) Applicants: Mayo Foundation for Medical Education and Research, Rochester, MN (US); Vyriad, Inc., Rochester, MN (US)

(72) Inventors: Luke Russell, Rochester, MN (US); Kah-Whye Peng, Rochester, MN (US); Stephen James Russell, Rochester, MN (US)

(73) Assignees: Mayo Foundation for Medical Education and Research, Rochester, MN (US); Vyriad, Inc., Rochester, MN (US)

( * ) Notice: Subject to any disclaimer, the term of this patent is extended or adjusted under 35 U.S.C. 154(b) by 1248 days.

(21) Appl. No.: 17/598,510

(22) PCT Filed: Mar. 27, 2020

(86) PCT No.: PCT/US2020/025409

§ 371 (c)(1),
(2) Date: Sep. 27, 2021

(87) PCT Pub. No.: WO2020/198652

PCT Pub. Date: Oct. 1, 2020

(65) Prior Publication Data

US 2022/0178910 A1 Jun. 9, 2022

Related U.S. Application Data

(60) Provisional application No. 62/825,482, filed on Mar. 28, 2019.

(51) Int. Cl.
*G01N 33/50* (2006.01)
*G01N 33/575* (2026.01)
*G01N 33/68* (2006.01)

(52) U.S. Cl.
CPC ... *G01N 33/5017* (2013.01); *G01N 33/57557* (2026.01); *G01N 33/6866* (2013.01); *G01N 2333/565* (2013.01); *G01N 2800/52* (2013.01)

(58) Field of Classification Search
None
See application file for complete search history.

(56) References Cited

U.S. PATENT DOCUMENTS 6,428,968 B1 * 8/2002 Molnar-Kimber ... A61K 31/704 435/5
2018/0237492 A1 * 8/2018 Russell ................ C07K 14/705

FOREIGN PATENT DOCUMENTS

WO WO 2012/031137 3/2012
WO WO 2013/112942 8/2013
WO WO 2017/218757 12/2017
WO WO-2017218757 A1 * 12/2017 ........... A61K 35/766
WO WO 2018/078220 5/2018
WO WO 2018/132571 7/2018

OTHER PUBLICATIONS

Waiker et al (J Am Soc Nephrol. Jan. 2012; 23(1): 13-21) (Year: 2012).*
Brooks (Genome Res. Feb. 2012;22(2):183-7) (Year: 2012).*
Shalhout et al (Nat Rev Clin Oncol. Mar. 2023;20(3):160-177. Epub Jan. 11, 2023) (Year: 2023).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Bork (Genome Research, 2000, 10:398-400) (Year: 2000).*
Kulmanov et al (Bioinformatics, 34(4), 2018, 660-668) (Year: 2018).*
Vajdos et al. (J Mol Biol. Jul. 5, 2002;320(2):415-28) (Year: 2002).*
Brown et al. (J Immunol. May 1996;156(9):3285-91) (Year: 1996).*
Guido et al (Curr Med Chem. 2008; 15(1):37-46) (Year: 2008).*
Clark et al (J. Med. Chem., 2014, 57 (12), pp. 5023-5038) (Year: 2014).*
Aagaard et al (Advanced Drug Delivery Reviews 59 (2007) 75-86) (Year: 2007).*
Warzocha et al (Leukemia and Lymphoma (1997) vol. 24. pp. 267-281) (Year: 1997).*
McKeague et al (J Nucleic Acids. 2012;2012:748913. Epub Oct. 24, 2012) (Year: 2012).*
Gupta et al (Perspect Clin Res. Jan. 2011;2(1):13-22) (Year: 2011).*
Extended Search Report in European Appln. No. 20776725.2, dated Nov. 21, 2022, 6 pages.
Merchan, "1338P: Tracking VSV-IFNβ-NIS oncolytic virus (OV) activity in patients (pts) with advanced solid tumors: The iodide symporter gene (NIS) as a pharmacodynamic (PD) marker using SPECT/CT imaging of OV therapy," Ann. Oncology, Oct. 1, 2018, 29(S8):viii479-viii480.
Andtbacka et al., "Talimogene Laherparepvec Improves Durable Response Rate in Patients With Advanced Melanoma," J. Clin. Oncology, Sep. 1, 2015, 33(25):2780-2788.
Cripe et al., "Abstract CT090: Rational design of an oncolytic virus permits use of interferon beta as a pharmacodynamic marker for clinical application," Abstract, Presented at Proceedings of the AACR Annual Meeting 2019, Atlanta, GA, USA, Mar. 29-Apr. 3, 2019; Cancer Research, Jul. 1, 2019, 79(13_Supplement):CT090, 4 pages.
Gen Bank Accession No. NC_001560.1, "Vesicular stomatitis Indiana virus, complete genome," dated Aug. 13, 2018, 8 pages.

(Continued)

*Primary Examiner* — Brian Gangle
*Assistant Examiner* — Andrea K McCollum
(74) *Attorney, Agent, or Firm* — Fish & Richardson P.C.

(57) ABSTRACT

The present invention generally relates to pharmacokinetic and pharmacodynamics markers for cancer therapeutic regimens and methods of treating cancer. Oncolytic virus probes that comprise a nucleic acid encoding soluble interferon beta (IFNβ) and methods for use thereof are provided.

19 Claims, 9 Drawing Sheets

(56) References Cited

OTHER PUBLICATIONS

PCT International Preliminary Report on Patentability in International Appl. No. PCT/US2020/025409, dated Sep. 28, 2021, 8 pages.

PCT International Search Report and Written Opinion in International Appln. No. PCT/US2020/025409, dated Jun. 19, 2020, 10 pages.

Peng et al., "Rational design of an oncolytic virus (OV) permits use of interferon beta as a pharmacodynamic marker for clinical application," Poster, Presented at Proceedings of the AACR Annual Meeting 2019, Atlanta, GA, USA, Mar. 29-Apr. 3, 2019, 1 page.

LeBlanc et al., "Safety studies on intravenous administration of oncolytic recombinant vesicular stomatitis virus in purpose-bred beagle dogs," Hum. Gene Ther. Clin. Dev., Dec. 2013, 24(4):174-81.

Naik et al., "Curative one-shot systemic virotherapy in murine myeloma," Leukemia, Aug. 2012, 26(8):1870-1878.

Powell et al., "VSV-IFNβ-NIS intratumoral (IT) injection: A first-in-human (FIH), phase I study of an innovative oncolytic virotherapy, alone and with an anti-PD-L1 antibody, in patients with refractory solid tumors," Ann. Oncology, Oct. 2018, 29(S8):viii439.

ClinicalTrials.gov [online], "VSV-hIFNbeta-NIS With or Without Cyclophosphamide or Ipilimumab and Nivolumab in Treating Patients With Relapsed or Refractory Multiple Myeloma, Acute Myeloid Leukemia or Lymphoma," NCT03017820, last updated May 6, 2023, retrieved on Jun. 2, 2023, retrieved from URL <https://clinicaltrials.gov/ct2/show/NCT03017820>, 41 pages.

* cited by examiner

Serum IFNβ (Dose Level 1-2, 3x10^6-1x10^7 TCID50)

Serum IFNβ (Dose Level 3, 3x10^7 TCID50)

Serum IFNβ (Dose Level 4, 1x10^8 TCID50)

Serum IFNβ (Dose Level 5, 3x10^8 TCID50)

Serum IFNβ (Dose Level 6, 1x10^9 TCID50)

Serum IFNβ (Dose Level 7, 3x10^9 TCID50)
Serum IFNB (pg/mL)
Day
DL1 102-001 102-002 102-003
DL2 102-004 104-007 104-009
103-014 103-015 105-011 105-012
104-017 104-019 105-016 105-020
105-021 106-022 104-023 104-030
103-025 105-026 105-027 102-028 103-029 106-032
102-033 105-038 104-039

T cell lymphoma

| Location | Baseline | D23 |
|---|---|---|
| Eye right | 0.7 x 0.3 | 0 |
| Arm left | 3 x 2 | 0 |
| Arm right | 2 x 1 | 1 x 1 |
| Right medial thigh | 4 x 2.5 | 3.5 x 1 |
| **Total cm2** | **18.21** | **4.6** |

75% reduction in tumor diameters

IFNβ AS A PHARMACODYNAMIC MARKER IN VSV-IFNβ-NIS ONCOLYTIC THERAPY

CROSS-REFERENCE TO RELATED APPLICATIONS

This application is a National Stage application under 35 U.S.C. § 371 of International Application No. PCT/US2020/025409, having an International Filing Date of Mar. 27, 2020, which claims priority to U.S. Provisional Application Ser. No. 62/825,482, filed on Mar. 28, 2019. The disclosure of the prior application is considered part of the disclosure of this application, and is incorporated in its entirety into this application.

STATEMENT OF GOVERNMENTAL INTEREST

This invention was made with government support under CA015083 awarded by the National Institutes of Health. The government has certain rights in the invention.

BACKGROUND OF THE INVENTION

The present invention generally relates to pharmacokinetic and pharmacodynamics markers for therapeutic regimens and methods of treating cancer.

Cancer remains among the leading causes for death worldwide. In 2015, an estimated 1,658,370 new cases of cancer were diagnosed and 589,430 cancer deaths occurred in the USA. The five-year relative survival rates for all cancer diagnoses in years 2004-2010 was only 68%. Moreover, some cancers have particularly dim prognosis with 5-year relative survival rates of 7% for pancreatic cancer and less than 20% for liver, lung and esophageal cancers; rates for advanced stage malignancies with distant metastases range from 2% for pancreatic cancer to 55% for thyroid cancer.

Chemotherapy is the standard treatment option for the majority of patients with metastatic and/or advanced cancer. Unfortunately, for many patients, chemotherapy is not curative and their disease will become refractory to therapy. Patients with refractory, metastatic solid tumors have few treatment options.

Cancer immunotherapy is a rapidly emerging therapeutic class that offers the potential for clinical benefit when chemotherapy becomes ineffective. Over the past decade, immune checkpoint inhibitors such as ipilimumab, pembrolizumab, atezolizumab and nivolumab have been approved. These approvals were initially for melanoma, but have more recently expanded to other disease types, and additional agents have recently been approved including avelumab and durvalumab. These agents have stimulated the resurgence of immunotherapies in the clinical pipeline. Numerous agents are in development, including oncolytic viral therapy.

Oncolytic virotherapy is a promising alternative to chemotherapy, especially in patients with refractory or recurrent diseases who have failed more than one line of previous cancer therapies. The therapeutic efficacy of oncolytic viruses is determined by their ability to invoke a multifaceted attack. Oncolytic viruses selectively replicate in cancer cells, and while inducing pro-inflammatory cellular lysis and exposure of tumor-associated antigens, they help reverse microenvironment immune suppression and reinvigorate host effector cells to encourage systemic, durable anticancer immunity.

In 2015, the first oncolytic viral therapy, Imlygic (talimogene Laherparepvec), was approved for use in patients with locally advanced melanoma. To further understand their safety and efficacy, oncolytic viruses must be evaluated in patients with refractory, solid tumors. Recently, T-Vec, an oncolytic herpes simplex type 1 virus encoding the granulocyte macrophage colony-stimulating factor, was approved by the FDA for treatment of surgically unresectable melanoma, making it the first in class approved in the USA (Andtbacka 2015). Three other phase III trials studying oncolytic virotherapy are underway: intratumoral administration of oncolytic vaccinia virus encoding GMCSF (Pexa-Vec) for treatment of hepatocellular carcinoma, intravesical adenovirus also encoding GMCSF (CG0070) for treatment of urinary bladder cancer and IV reovirus (Reolysin) treatment for head and neck cancer. Among other oncolytic viral clinical trials, a phase 1 study using intratumoral administration of an oncolytic VSV expressing IFNβ (and not expressing a symporter) for treatment of hepatocellular carcinoma is open and recruiting.

Oncolytic virotherapy can also be combined with other cancer therapies, such as chemotherapy or immunotherapy. Emerging data suggest that the use of checkpoint inhibitors in conjunction with oncolytic viruses can enhance the antitumor immune response through release of neoantigens, leading to durable objective responses in a larger proportion of patients than would be expected with the checkpoint inhibitor alone. While some studies suggest that the combination of checkpoint inhibitors and oncolytic viruses may be useful, to date there has been no study examining a combination therapy composed of a checkpoint inhibitor and an oncolytic virus for metastatic colon cancer in humans.

Oncolytic virotherapy can be optimized or customized. For example, cancer cells with an anti-viral deficiency can be identified based on the presence of a virotherapy permissive gene expression signature. One such set of markers is shown in WO 2017218757 A1. Gene expression signatures of the tumor will give actionable information. However, it is static, and therefore cannot take into account changing circumstances that may arise during treatment. In addition, gene expression signature cannot factor in tumor burden.

Thus, there is a need for real time measurement and monitoring in a dynamic clinical environment, and adapting the treatment decisions based on the individual response and changing circumstances in each patient.

SUMMARY OF THE INVENTION

The present invention generally relates to a method of diagnosis. In certain embodiments, the invention relates to methods of determining the likelihood that a cancerous tissue in a subject having the cancerous tissue will respond to administration of a cancer therapy regimen is provided. The methods generally comprise (a) administering intratumorally to the cancerous tissue a subtherapeutic diagnostic dose of an oncolytic virus probe that comprises a nucleic acid that codes for soluble interferon beta (IFNβ), and (b) measuring the circulating level of IFNβ in the subject after administration of the oncolytic virus to determine if the cancerous tissue is a strong responder, an intermediate responder, a low responder or a non-responder.

The present invention also relates to methods of treating a subject having been diagnosed with cancer. The treatment methods comprise: (a) administering to the subject a first dose of an oncolytic virus cancer therapy regimen that comprises a nucleic acid encoding interferon beta (IFNβ), and (b) administering at least a second dose of the oncolytic virus cancer therapy regimen if the subject has been identified as a strong responder or an intermediate responder to the oncolytic virus cancer therapy regimen.

BRIEF DESCRIPTION OF THE DRAWINGS

FIGS. 4A-4C show that the IFNβ level (the dark line) increases at 24 hours post administration. FIGS. 4D-4F show that the IFNα level (the dark line) decreases at 24 hours post administration. The data indicate that IFNβ transgene levels can serve as a biomarker of viral infection.

FIGS. 5A-5C show that the circulating levels of IFNβ can be detected in patients with intratumoral injection of doses in the range from approximately $10^{6}$ to $10^{8}$ TCID50.

FIG. 8 shows the CT scans of pre-treatment and 3 months after Voyager-V1 treatment in a subject with endometrial cancer. The overall tumor reduction is 16.5% in diameter at day 29. FIG. 8 shows there is a 75% reduction in tumor diameters in a subject with T-cell lymphoma.

DETAILED DESCRIPTION OF THE INVENTION

Figure 1:
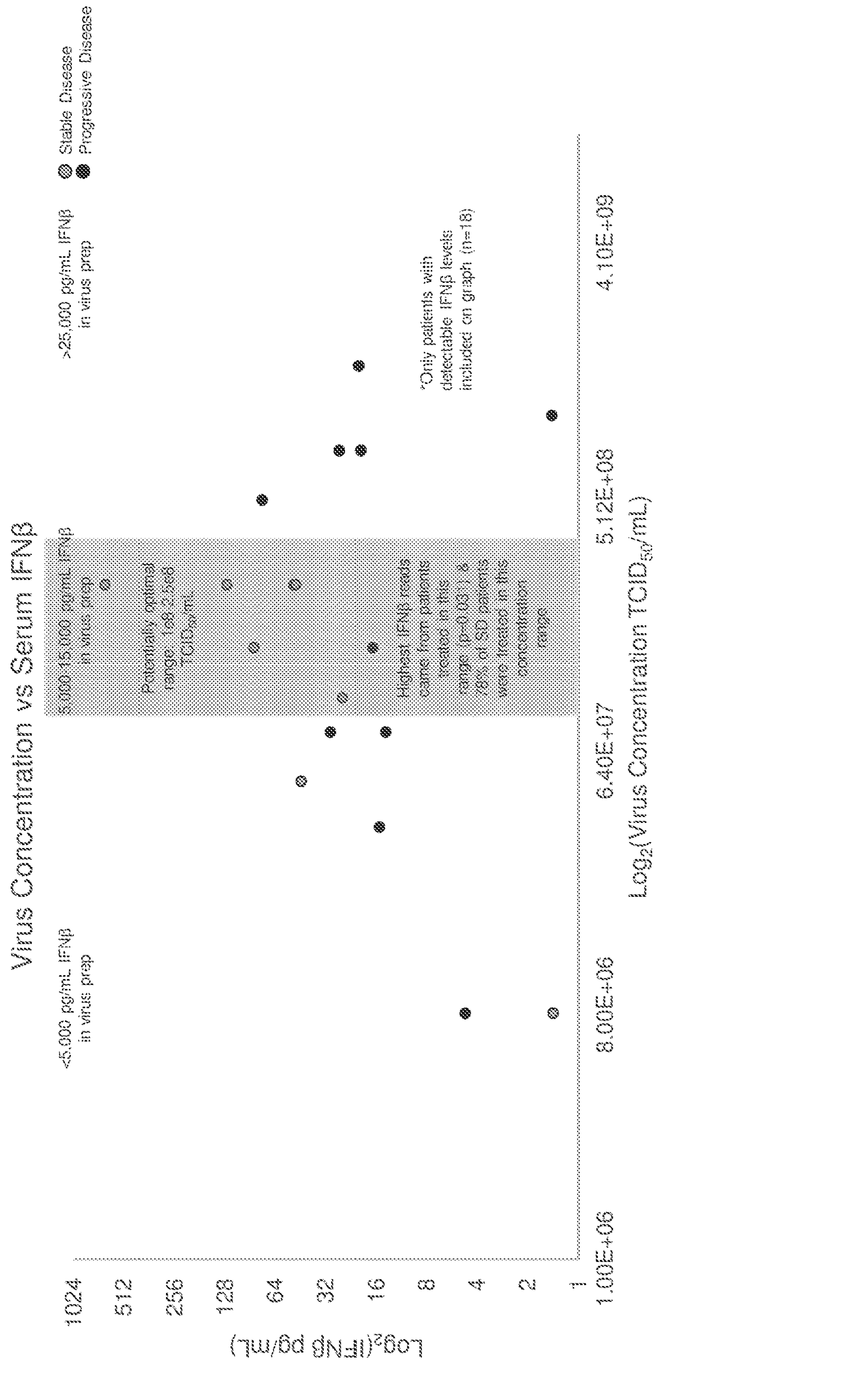
FIG. 1 shows that intratumorally injected Voyager-V1 virus concentration correlates with response. IFNβ levels predict patient's response to Voyager-V1.

The present invention generally relates to a method of diagnosis. In certain embodiments, the invention relates to methods of determining the likelihood that a cancerous tissue in a subject having the cancerous tissue will respond to administration of a cancer therapy regimen is provided. The methods generally comprise (a) administering intratumorally to the cancerous tissue a subtherapeutic diagnostic dose of an oncolytic virus probe that comprises a nucleic acid that codes for soluble interferon beta (IFNβ), and (b) measuring the circulating level of IFNβ in the subject after administration of the oncolytic virus to determine if the cancerous tissue is a strong responder, an intermediate responder, a low responder or a non-responder.

In certain embodiments, the cancer therapy regimen of the method comprises the oncolytic virus probe that is administered intratumorally in (a). In certain embodiments, the cancer therapy regimen of the method comprises a different oncolytic virus probe than what is administered intratumorally in (a). In certain embodiments, the cancer therapy regimen is an immuno-oncolytic therapy. In certain embodiments, the cancer therapy regimen is an antibody or small molecule anti-cancer treatment.

In certain embodiments, the oncolytic virus probe that is administered at a non-toxic and non-therapeutic. In certain embodiments, the non-therapeutic and non-toxic dose is from about $10^{5}$ TCID50 to about $3\times10^{9}$ TCID50. In certain embodiments, the non-therapeutic and non-toxic dose is from about $10^{8}$ TCID50 to about $5\times10^{8}$ TCID50.

In other embodiments, the oncolytic virus probe can be any GMP grade virus. In certain embodiments, the oncolytic virus probe is vesicular stomatitis virus (VSV). In certain embodiments, the oncolytic virus probe further comprises a nucleic acid encoding a sodium iodine symporter (NIS). In certain embodiments, the oncolytic virus probe has the construct of N-P-M-IFNβ-G-NIS-L.

In certain embodiments, the circulating level of IFNβ are measured in the subject between about 12 hours to about 45 days after administration of the oncolytic virus. In certain embodiments, the circulating level of IFNβ are measured in the subject between about 12 hours to about 3 days after administration of the oncolytic virus. In certain embodiments, the circulating level of IFNβ are measured in the subject about 48 hours after administration of the oncolytic virus. In certain embodiments, the circulating level of IFNβ are measured in the subject about 24 hours after administration of the oncolytic virus.

In certain embodiments, the circulating level of IFNβ is measured by an immunological assay.

In certain embodiments, the cancerous tissue is a solid tumor or a hematological malignancy. In certain embodiments, the cancerous tissue is a head and neck cancer, colon cancer, rectal cancer, pancreatic cancer, bladder cancer, breast cancer, hepatocellular cancer, lung cancer, medulloblastoma, atypical teratoid/rhabdoid tumor, a leukemia, a lymphoma, or a myeloma.

The present invention also relates to methods of treating a subject having been diagnosed with cancer. The treatment methods comprise: (a) administering to the subject a first dose of an oncolytic virus cancer therapy regimen that comprises a nucleic acid encoding interferon beta (IFNβ), and (b) administering at least a second dose of the oncolytic virus cancer therapy regimen if the subject has been identified as a strong responder or an intermediate responder to the oncolytic virus cancer therapy regimen.

In certain embodiments, the cancer therapy regimen comprises administration of more than one anti-cancer composition. In certain embodiments, the cancerous tissue is a solid tumor and the cancer therapy regimen is an oncolytic virus that is administered intratumorally at a dose that is based upon the number of viral particles per unit volume of tumor.

In certain embodiments, the therapeutic dose of the oncolytic virus to be administered intratumorally is given in a standard dose range. In certain embodiments, the cancer therapy regimen is an oncolytic virus that is administered intravenously.

In certain embodiments, the first dose of the oncolytic virus cancer therapy regimen is an intravenous administration. In certain embodiments, the first dose of the oncolytic virus cancer therapy regimen is an intratumoral administration. In certain embodiments, the first dose of the oncolytic virus cancer therapy regimen is a non-therapeutic dose and non-toxic dose of the oncolytic virus cancer therapy regimen. In certain embodiments, the second dose of the oncolytic virus cancer therapy regimen is an intravenous administration or an intratumoral administration.

In certain embodiments, the oncolytic virus cancer therapy regimen comprises a nucleic acid encoding a sodium iodine symporter (NIS). In certain embodiments, the oncolytic virus is an RNA virus. In certain embodiments, the oncolytic virus is a vesicular stomatitis virus (VSV). In certain embodiments, the VSV has the construct of N-P-M-IFNβ-G-NIS-L.

In certain embodiments, the method of treatment further comprises administrating one or more additional immune-oncology therapy agents to the subject if the subject has been identified as an intermediate responder to the oncolytic virus cancer therapy regimen.

In certain embodiments, the method of treatment further comprises administrating a janus kinase inhibitor (JAK inhibitor) inhibitor to the subject if the subject has been identified as a strong responder to the oncolytic virus cancer therapy regimen. In certain embodiments, the JAK inhibitor is ruxolitinib.

In certain embodiments, the level of IFNβ is assessed between about 0.5 to 45 days after administration of the first dose of the oncolytic virus cancer therapy regimen. In certain embodiments, the level of IFNβ is assessed between about 0.5 to 3 days after administration of the first dose of the oncolytic virus cancer therapy regimen. In certain embodiments, the second dose of the oncolytic virus cancer therapy regimen is administered within about 1-10 days after administration of the first dose of the oncolytic virus cancer therapy regimen. In certain embodiments, the circulating levels of IFNβ are assessed within about 12-24 hours after administration of the first dose of the oncolytic virus cancer therapy regimen. In certain embodiments, the circulating level of IFNβ is assessed by an immunological assay.

In certain embodiments, the cancer is a solid tumor or a hematological malignancy. In certain embodiments, the solid tumor is a head and neck cancer, colon cancer, rectal cancer, pancreatic cancer, bladder cancer, breast cancer, hepatocellular cancer, lung cancer, medulloblastoma, or atypical teratoid/rhabdoid tumor. In certain embodiments, the hematological malignancy is a leukemia, a lymphoma, or a myeloma.

In certain embodiments, the second administration of the oncolytic virus cancer therapy regimen is by intratumoral injection. In certain embodiments, in the second intratumoral injection is administered to the subject based on the number of viral particles per unit volume of tumor. In certain embodiments, wherein second intratumoral injection is administered to the subject in a standard dose range. In certain embodiments, the therapeutic dose of an oncolytic virus is administered intravenously.

The present invention generally relates to methods of diagnosis and treating cancer. In certain embodiments, the present invention provides a method for early assessment of an individual patient's response to cancer therapy and adapting the treatment decisions based on the individual response and changing circumstances in each patient. In certain embodiments, the present invention provides a method to interrogate a cancerous tissue's microenvironment and potential immune response to a cancer therapeutic agent in an individual patient. Such a method can inform the choice of the most effective therapeutic regimen tailored for the specific individual.

A "sample," "test sample," or "biological sample" as used interchangeably herein is of biological origin, in specific embodiments, such as from a mammal. In certain examples, the sample is a tissue or body fluid obtained from a subject. In other certain examples, the sample is a human sample or animal samples. Non-limiting sources of a sample include blood, plasma, serum, urine, spinal fluid, lymph fluid, synovial fluid, cerebrospinal fluid, tears, saliva, milk, mucosal secretion, effusion, sweat, biopsy aspirates, ascites or fluidic extracts. In a specific example, the sample is a fluid sample. In a specific example, the sample is a cancerous tissue. In some embodiments, samples are derived from a subject (e.g., a human) comprising different sample sources described herein. In some embodiments, the samples are subject to further processing. Exemplary procedures for processing samples are provided throughout the application, for instance, in the Example section.

The term "subject" refers to any animal, e.g., a mammal, including, but not limited to humans and non-human primates, which is to be the recipient of a particular treatment.

As used herein, a subtherapeutic dose means a dose level or a dose range that is lower than a dose level or range that would normally be administered for a certain indication, or a certain individual. In certain embodiments, a subtherapeutic dose is a dose level or range that is lower than what is on the label of agent, such as any cancer therapeutic agent. In certain embodiments, a subtherapeutic dose means a dose level or a dose range that does not elicit toxicity or a therapeutic response in a subject. In certain embodiments, the subtherapeutic dose is a non-toxic and non-therapeutic dose.

An oncolytic virus as used herein means a virus that infects and kills cancer cells through normal viral replication and lifecycle but not normal cells. In some examples, an oncolytic virus therapy may make it easier to kill tumor cells with other cancer therapies, such as chemotherapy and radiation therapy. an oncolytic virus therapy is a type of targeted therapy. It is also called oncolytic virotherapy, viral therapy, and virotherapy, which are used interchangeably herein.

An oncolytic virus probe as used herein means an oncolytic virus that is used in a lower dose than it would be used as a therapeutic agent to interrogate a cancerous tissue, such as a tumor, for the cancerous tissue's specific characteristics, such as immune responses to the virus, the tissue or tumor microenvironment, or the defense capacity of the cancerous tissue. In some embodiments, the oncolytic virus probe is used to investigate an individual subject who has been diagnosed with cancer. The oncolytic virus probe can be any GMP grade virus. In certain embodiments, the oncolytic virus probe is vesicular stomatitis virus (VSV). In certain embodiments, the oncolytic virus probe further comprises a nucleic acid encoding a sodium iodine symporter (NIS). In some embodiments, the probe is a virus that would be therapeutic if provided at sufficient doses.

In certain embodiments, the subtherapeutic dose of the oncolytic virus probe is from about $10^5$ TCID50 to about $3\times10^9$ TCID50. In certain embodiments, the subtherapeutic dose is from about $10^8$ TCID50 to about $5\times10^8$ TCID50. In certain embodiments, the subtherapeutic dose of the oncolytic virus probe can be calculated by any person skilled in the art using a standard method.

In certain embodiments, the oncolytic virus probe has the construct of N-P-M-IFNβ-G-NIS-L. In certain embodiments, the non-therapeutic and non-toxic dose of the oncolytic virus probe is from about $10^5$ TCID50 to about $3\times10^9$ TCID50. In certain embodiments, the non-therapeutic and non-toxic dose is from about $10^8$ TCID50 to about $5\times10^8$ TCID50.

The term "circulating level" is intended to refer to the amount or concentration of a marker present in a circulating fluid. Circulating levels can be expressed in terms of, for example, absolute amounts, concentrations, amount per unit mass of the subject, and can be expressed in terms of relative amounts. The level of a marker may also be a relative amount, such as but not limited to, as compared to an internal standard, or baseline levels, or can be expressed as a range of amount, a minimum and/or maximum amount, a mean amount, a median amount, or the presence or absence of a marker.

In certain embodiments, the circulating level of IFNβ are measured in the subject prior to the administration of an oncolytic virus. The oncolytic virus can be a virus probe administered at a subtherapeutic dose, or a viratherapy agent. In certain embodiments, the circulating level of IFNβ are measured in the subject between about 12 hours to about 45 days after administration of the oncolytic virus. In certain embodiments, the circulating level of IFNβ are measured in the subject between about 12 hours to about 3 days after administration of the oncolytic virus. In certain embodiments, the circulating level of IFNβ are measured in the subject about 48 hours after administration of the oncolytic virus. In certain embodiments, the circulating level of IFNβ are measured in the subject about 24 hours after administration of the oncolytic virus. The levels of circulating IFNβ in a subject identifies the subject as a strong responder, an intermediate responder, a low responder or a non-responder to the administration of an oncolytic virus.

The levels of circulating IFNβ in a strong responder, an intermediate responder, a low responder, or a non-responder are determined by more than one factors and may overlap. For instance, the actual amount of IFNβ produced in a subject will depend on the type of viral vector used, the marker gene or protein carried by the vector, the initial dose given, the individual's tumor microenvironment, and the individual's immune defense mechanism. The marker gene or protein used here means a gene or protein whose levels, i.e., circulating or expression level, can be detectable by common techniques. In some embodiments, it is a soluble IFNβ. In some embodiments, it is a NIS.

In the instance of a soluble IFNβ expressed by a VSV virus, such as Voyager-V1, a circulating IFNβ level between 0-100 pg/ml may be considered low, depending on the initial dose of probe, and identifies a subject a low responder or non-responder. In some embodiments, a circulating IFNβ level of 10 pg/ml and above may be high, depending on the initial dose of probe, and identifies a subject a strong responder. However, different initial dosages will elicit different high and low ranges.

The term "cancer" has its common meaning in the art. Generally, cancer is a term for diseases in which abnormal cells divide without control and can invade nearby tissues. There are several main types of cancer. For example, carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord. Also called malignancy. Cancer as used herein include all types of cancers, whether it is a solid tumor or a blood cancer and regardless the origin of the cancer. In some embodiments, the cancer is a head and neck cancer, colon cancer, rectal cancer, pancreatic cancer, bladder cancer, breast cancer, hepatocellular cancer, lung cancer, medulloblastoma, atypical teratoid/rhabdoid tumor, a leukemia, a lymphoma, or a myeloma.

A cancerous tissue means a tissue that has identifiable cancer cells. In some embodiments, the cancerous tissue is a solid tumor.

The administration as used herein include any method for giving a medication to a subject, including but not limited to intratumoral and intravenous. An intravenous (IV) injection, or infusion, means that the medication sent directly into the subject's vein using a needle or tube. In some embodiment, a thin plastic tube called an IV catheter is inserted into the vein. An intratumoral administration means that a medication is given directly within a tumor or a cancerous tissue.

The present invention also relates to pharmacodynamics (PD) markers for therapeutic regimens and methods of treating cancer, with the methods comprising administering to the subject a recombinant vesicular stomatitis virus that has been engineered to expresses interferon beta and a sodium iodine symporter (e.g., VSV-IFNβ-NIS). In the present invention, the terms subject and patient are used interchangeably.

Human infection with wild type VSV is usually asymptomatic, but can cause an acute, febrile, influenza like illness lasting 3-6 days characterized by fever, chills, nausea, vomiting, headache, retrobulbar pain, myalgia, substernal pain, malaise, pharyngitis, conjunctivitis and lymphadenitis. Complications are generally not seen in humans infected with wild type VSV and fatalities have not been recorded, although a published case of nonfatal meningoencephalitis in a 3-year-old Panamanian child was attributed to VSV infection. A modified Indiana strain VSV has been used in over 17,000 healthy volunteers in an Ebola vaccination program, leading researchers to conclude that the safety profile is considered acceptable in healthy adults. The VSV-based vaccine is generally well tolerated and there have been few vaccine-related adverse events reported. Common adverse events include headache, pyrexia, fatigue, and myalgia, of which the majority are mild to moderate and generally of short duration. Neither shedding of live virus nor human-to-human transmission have been seen.

The vesicular stomatitis virus is a member of the Rhabdoviridae family. The VSV genome is a single molecule of negative-sense RNA that encodes five major polypeptides: a nucleocapsid (N) polypeptide, a phosphoprotein (P) polypeptide, a matrix (M) polypeptide, a glycoprotein (G) polypeptide, and a viral polymerase (L) polypeptide. The nucleic acid sequences of a vesicular stomatitis virus provided herein that encode a VSV N polypeptide, a VSV P polypeptide, a VSV M polypeptide, a VSV G polypeptide and a VSV L polypeptide can be from a VSV Indiana strain as set forth in Gen Bank Accession Nos. NC_001560 (GI No. 9627229) or can be from a VSV New Jersey strain.

In one embodiment, the methods and regimens of the present invention comprise administration of Voyager-V1 (VSV-IFNβ-NIS, VV1). VSV-IFNβ-NIS is a live virus engineered to express both the human interferon β (hIFNβ) gene and the thyroidal sodium iodide symporter (NIS). The virus was constructed by inserting the hIFNβ gene downstream of the M gene and the NIS gene (cDNA) downstream of the gene for the G protein into a full-length infectious molecular clone of an Indiana strain vesicular stomatitis virus (VSV). VSV-IFNβ-NIS is described in PCT/US2011/050227, which is incorporated by reference. An illustration of the construct of Voyager-V1 is provided in FIG. 6.

EXAMPLES

Example 1

Voyager-V1 Systemic Virotherapy

Figure 6:
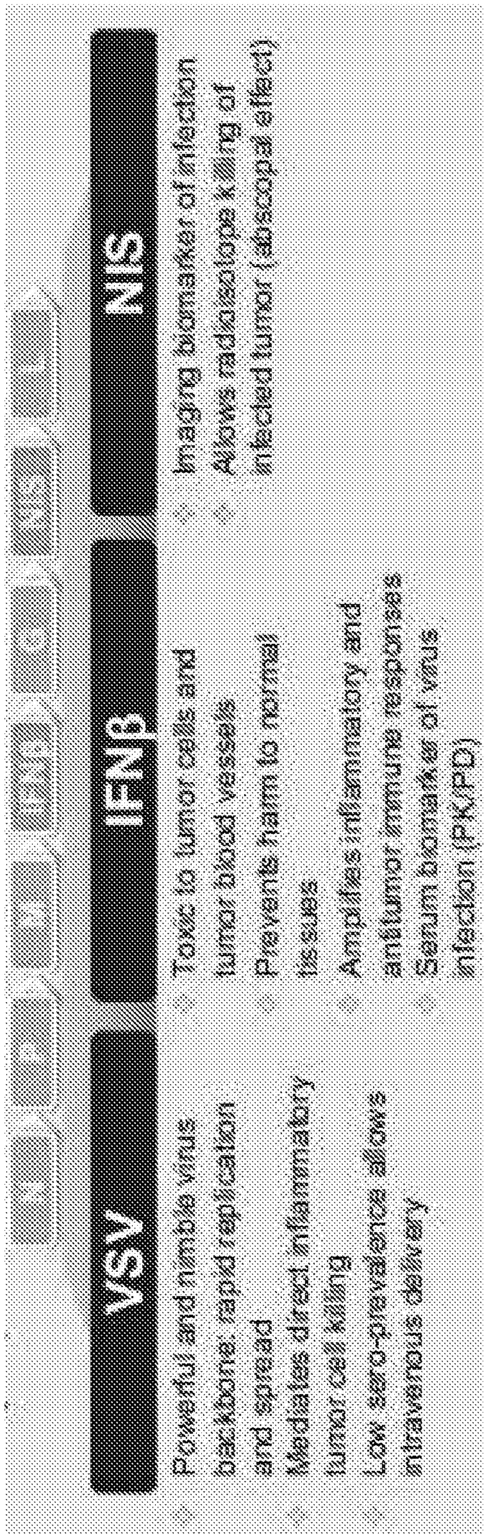
FIG. 6 shows an illustration of the construct of Voyager-V1 (VSV-IFNβ-NIS, VV1)

Voyager-V1 (VSV-IFNβ-NIS, VV1) is an armed and trackable oncolytic vesicular stomatitis virus (VSV) designed to selectively destroy tumor cells through direct oncolysis and immune activation. VV1 expresses human interferon beta (IFNβ) and the NIS sodium iodide symporter. During the study, it was discovered that IFNβ could also serve as a soluble biomarker to monitor viral replication in vivo. We report here the novel use of virus-encoded IFNβ using correlative data from three phase 1 trials of Voyager-V1 in patients with refractory cancers (n=51), with case studies demonstrating mechanism of action (MOA) of Voyager-V1. An illustration of the Voyager-V1 construct is shown in FIG. 6.

The primary objectives of this study include safety and tolerability of Voyager-V1 after intratumoral (IT) or intravenous (IV) administration in patients with relapsed or recurrent hematological malignancies or solid tumors.

Figure 7:
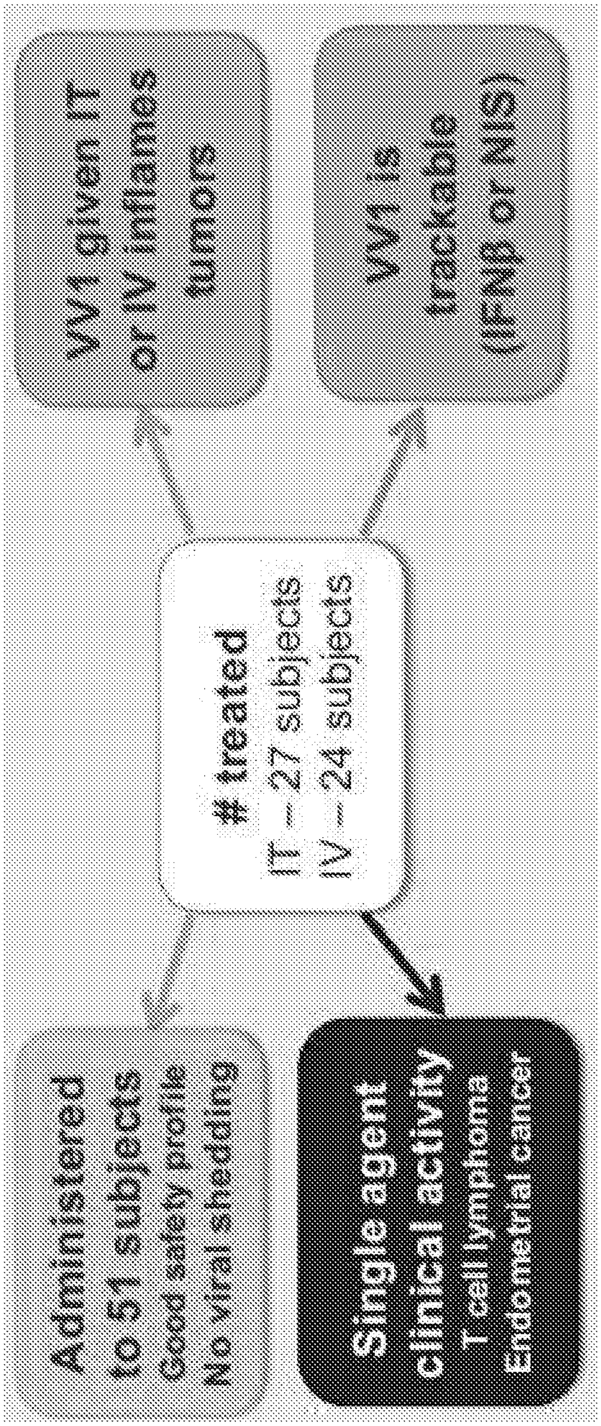
FIG. 7 shows a flow chart summary of the method used in the Voyager-V1 systemic virotherapy study as provided in Example 1.

The secondary objectives of this study include establishing proof of concept (e.g., by NIS imaging, immune activation, and tumor selectivity), PK and PD of Voyager-V1, viral shedding, immune responses, and response rate. A schematic flow chart of the study design is shown in FIG. 7.

Fifty-one patients received one dose of Voyager-V1 either IT or IV at doses ranging from $3\times10^6$ to $5\times10^{10}$ $TCID_{50}$.

Blood was collected before administration of virus (both IV and IT), 4 hours post-infusion (IV), day 2 (24-hour; both IT and IV), day 3, 8, and 15 (both IT and IV), day 22 (IV only) and day 29 (IT only). IFNβ levels were measured using a standard ELISA kit specific for human IFNβ (PBL Assay Science, NJ). Cytokine levels were tested using a multiple cytokine assay kit (R&D Systems, MN). Exemplary protocols are provided in Examples 3 and 4 below.

Figure 8:
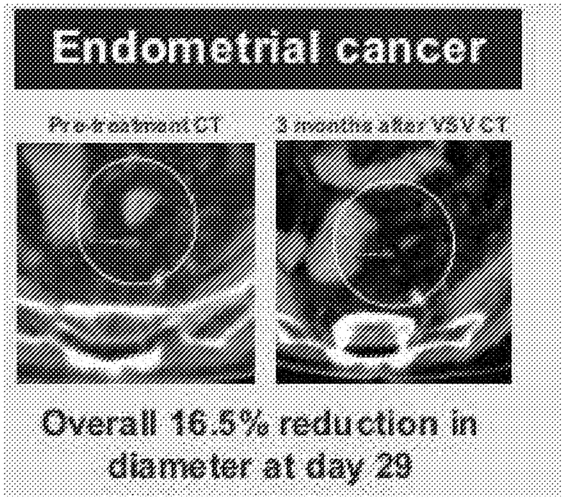
FIGS. 8 shows the clinical activity after one intravenous dose of Voyager-V1. Specifically.
Figure 9A:
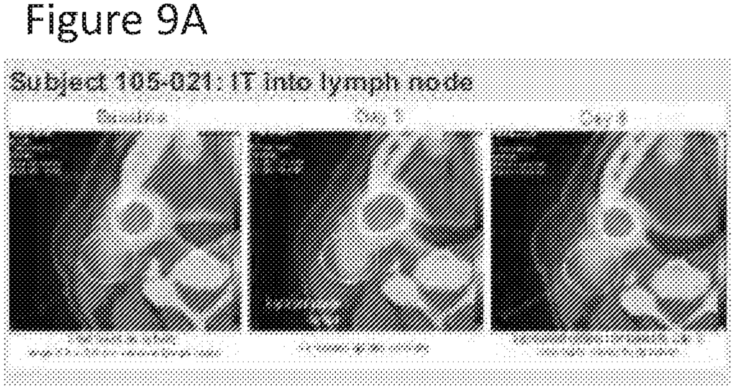
FIGS. 9A and 9B show that NIS imaging confirms infection of tumor by Voyager-V1 in two subject, Subject 105-021 (FIG. 9A) and Subject 105-020 (FIG. 9B).
Figure 9B:
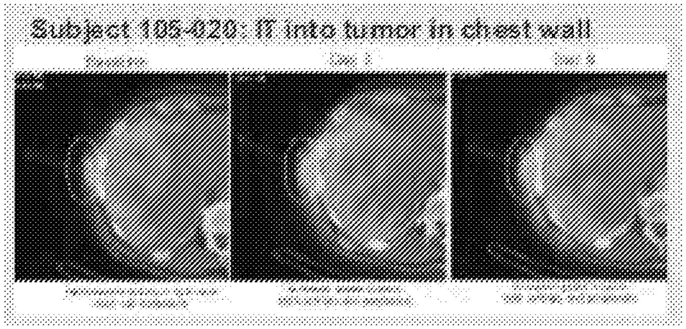
Figure 10A:
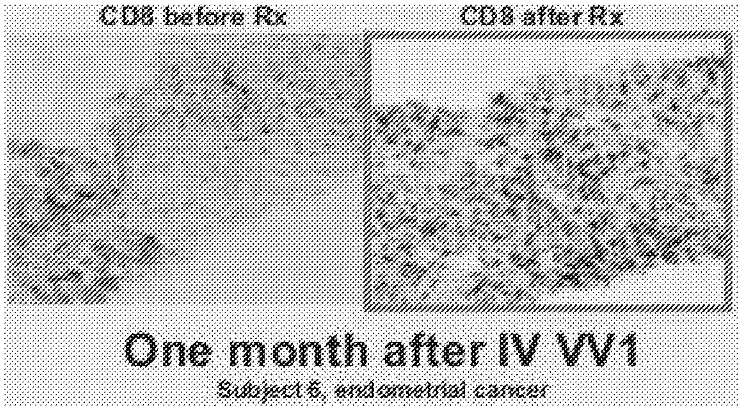
FIGS. 10A and 10B show that Voyager-V1 treatment increases CD8 tumor infiltrating cells one month after with intravenous injection (subject 6, FIG. 10A) or intratumoral injection (subject 103-014, FIG. 10B).
Figure 10B:
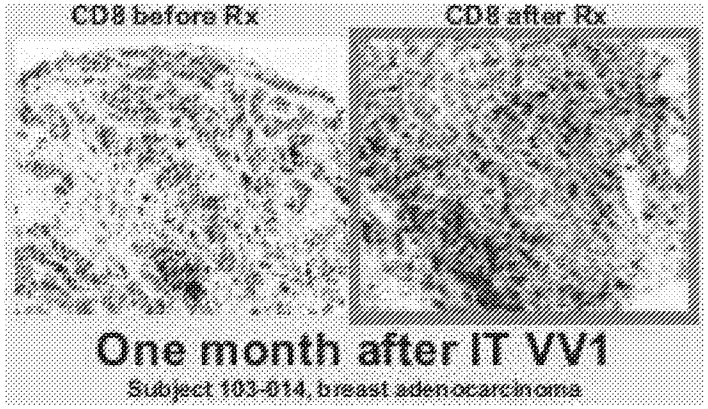

The efficacy of Voyager-V1 systemic virotherapy are exemplified in FIGS. 8, 9A, 9B, 10A, and 10B. Specifically, FIG. 8 shows the CT scans of pre-treatment and 3 months after Voyager-V1 treatment in a subject with endometrial cancer. The overall tumor reduction is 16.5% in diameter at day 29. FIG. 8 shows there is a 75% reduction in tumor diameters in a subject with T-cell lymphoma. FIGS. 9A and 9B show that NIS imaging confirms infection of tumor by Voyager-V1 in two subject, Subject 105-021 (FIG. 9A) and Subject 105-020 (FIG. 9B). FIGS. 10A and 10B show that Voyager-V1 treatment increases CD8 tumor infiltrating cells one month after with intravenous injection (subject 6, FIG. 10A) or intratumoral injection (subject 103-014, FIG. 10B).

Example 2

Virus Concentration Predicts Response

Patients with a variety of solid tumor indications were injected intratumorally with Voyager-V1. Voyager-V1 doses ranged from $3\times10^6$ to $3\times10^9$ TCID50, and injected volume ranged from 0.5-4.0 mL dependent upon the size of the injected lesion. Injected virus concentrations for n=27 patients ranged from $7.5\times10^5$ to $1.5\times10^9$ TCID50/mL, and contained some interferon beta in the injected volume (clinical product contains $8\times10^5$ to $1.2\times10^6$ pg/mL interferon beta, which is diluted during drug preparation at the on-site pharmacy). All patients had blood serum drawn on day 1 pre-treatment, and days 2, 3, 8, and 15 post-treatment. Serum IFNβ levels were evaluated at each time point, and peak serum interferon beta levels for all patients with detectable (>1.2 pg/mL) interferon beta were plotted against the concentration of injected virus for each patient (n=18). Peak serum IFNβ levels followed a bell curve with respect to injected virus concentration.

Highest IFNβ reads came from patients treated in the $1\times10^8$ to $2.5\times10^8$ TCID50/mL concentration range (student's 2-tailed T-test evaluating the peak interferon beta levels of patients treated within this concentration range (n=8) versus all other patients (n=19), P=0.031).

78% of stable disease (SD) patients were treated in the 1×108 to 2.5×108 TCID50/mL concentration range (9 patients had SD at 6 weeks post-Voyager-V1 therapy. Of these patients, 7/9 (78%) were treated in the 1×108 to 2.5×108 TCID50/mL concentration range).

Increasing concentrations of IFNβ in virus preparation may be inhibitory to virus replication. Average serum interferon beta levels measured at 24 hours post-Voyager-V1 administration increased from 2.0 pg/mL IFNβ at $7.5\times10^6$ TCID50/mL to 219.5 pg/mL IFNβ at $2.5\times10^8$ TCID50/mL (average), beyond which, peak IFNβ levels began to decline (77 pg/mL IFNβ at $5\times10^8$ TCID50/mL; 23 pg/mL IFNβ at $7.5\times10^8$ TCID50/mL, and 11 pg/mL IFNβ at $1\times10^9$ TCID50/mL and higher). Higher virus concentrations mean higher IFNβ concentrations in the injected virus preparation, which may inhibit virus growth and spread.

Figure 2:
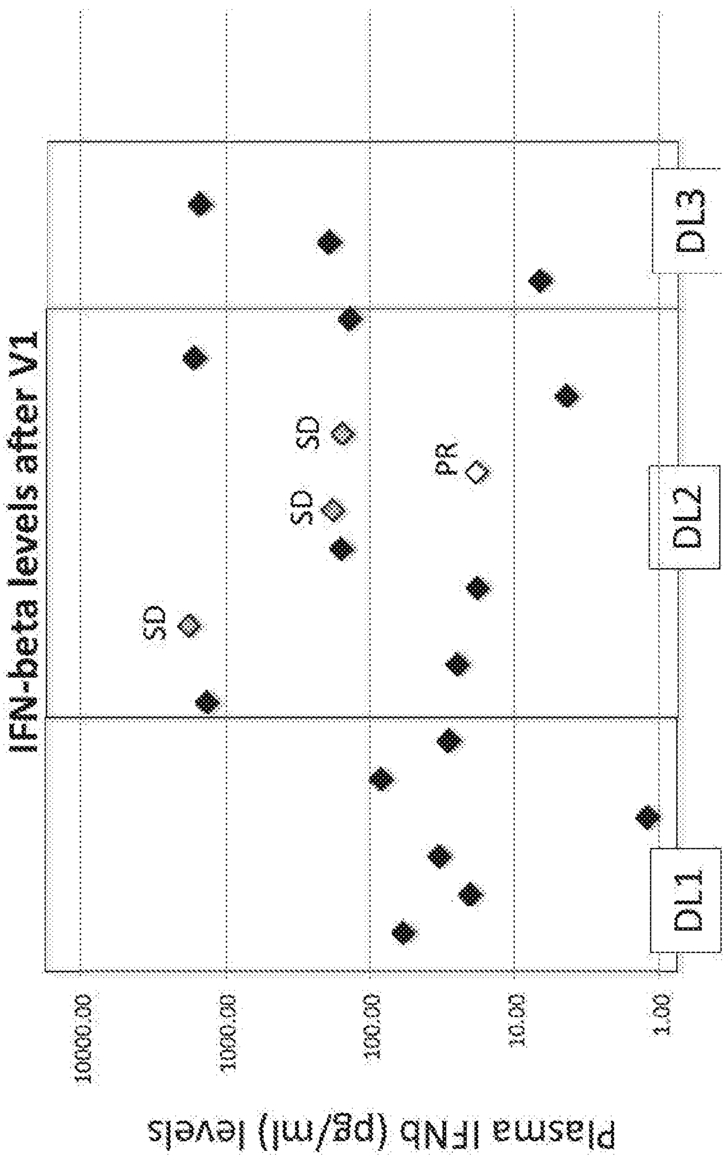
FIG. 2 shows the plasma INFβ levels in patients administered with dose level (DL) 1, 2, or 3 of Voyager-V1. DL1, DL2, and DL3 correspond to $5\times10^{9}$, $1.7\times10^{10}$, and $5\times10^{10}$ $TCID_{50}$, respectively. SD indicates stable disease. PR indicate partial response.

As shown in FIG. 1, the intratumorally injected Voyager-V1 virus concentration correlates at day 2 (24 hours post administration) with patients' response to the treatment. IFNβ levels predict patient's response to Voyager-V1. Patients with detectable levels of IFNβ tend to have stable disease. Further, FIG. 2 shows the plasma IFNβ levels at day 2 (24 h) in patients administered with one intravenous dose of Voyager-V1. The dose level (DL) 1, 2, or 3 of Voyager-V1. DL1, DL2, and DL3 correspond to $5\times10^9$, $1.7\times10^{16}$, and $5\times10^{16}$ $TCID_{50}$, respectively, of virus given by IV route to each subject. SD indicates stable disease. PR indicates partial response. Each diamond represents a single treated subject.

Figure 3:
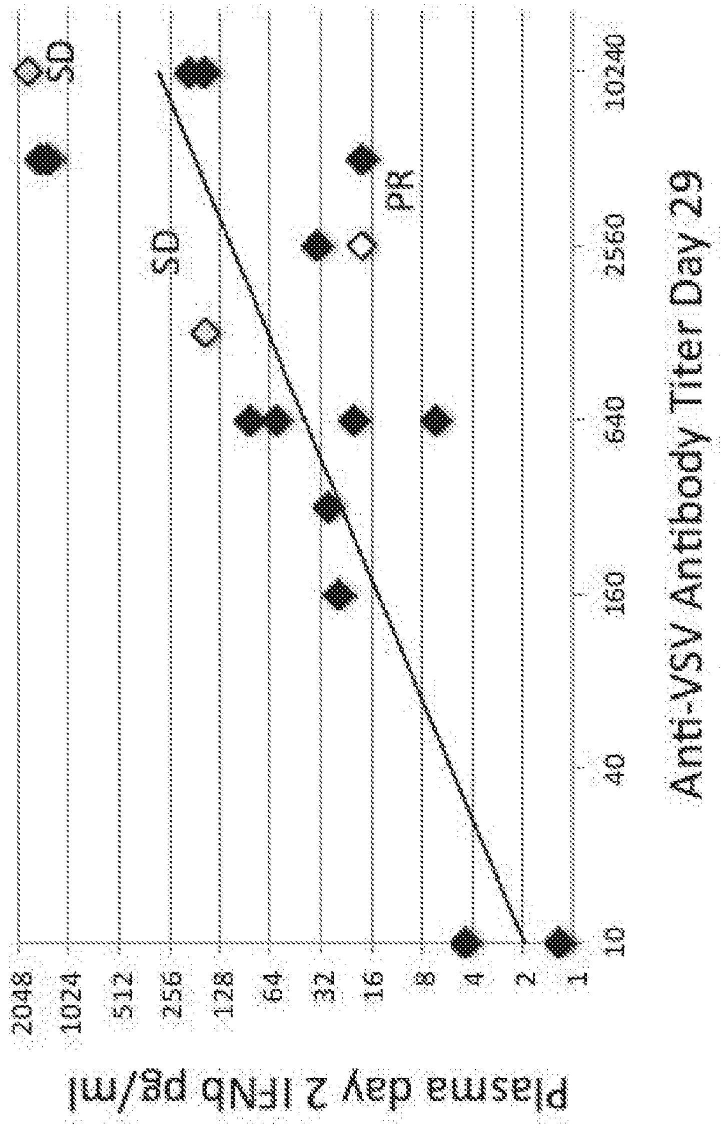
FIG. 3 shows a plot of plasma IFNβ level at day 2 (24 hours post administration) against anti-VSV antibody titer at day 29 (day 28 post administration).

VSV infection would result in adaptive host immune response and generates neutralizing antiviral antibodies (FIG. 3). Peak IFNβ level (day 2 shown in FIG. 3) correlates with anti-VSV antibody titers, indicating that IFNβ level early (24 h) after infusion of therapeutic virus would be a good indicator of Voyager-V1 viral replication and infection and permissiveness of the tumor to the virotherapy.

Figure 4A:
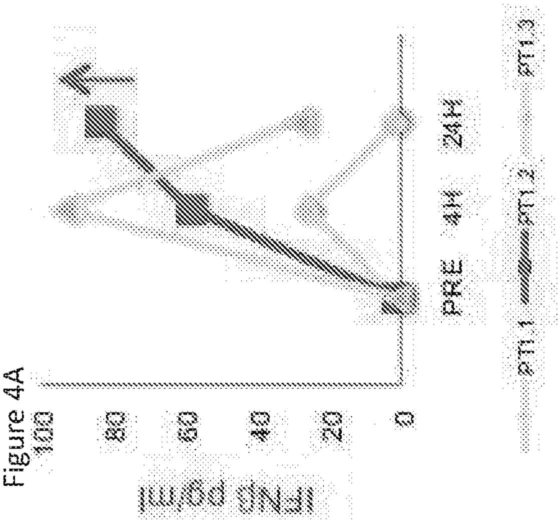
FIGS. 4A-4F show the comparison of relative IFNβ and IFNα trends in patients.
Figure 4B:
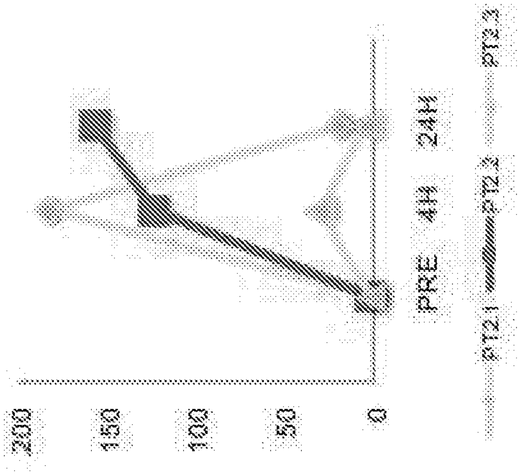
Figure 4C:
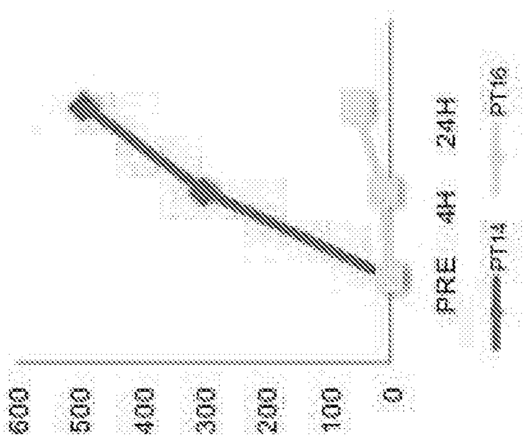
Figure 4D:
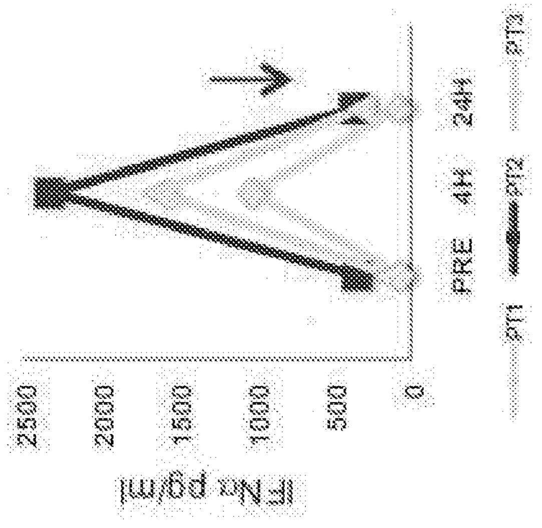
Figure 4E:
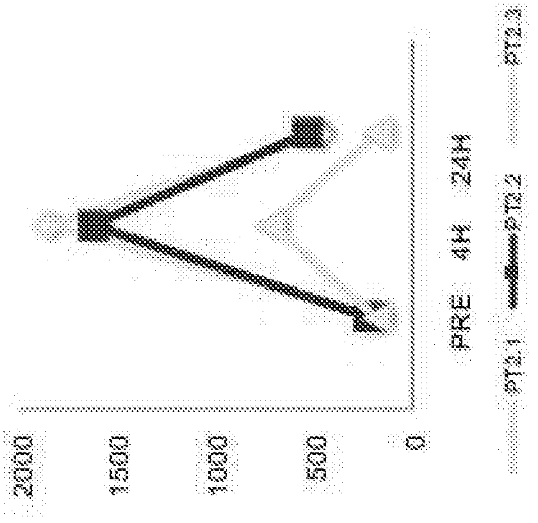
Figure 4F:
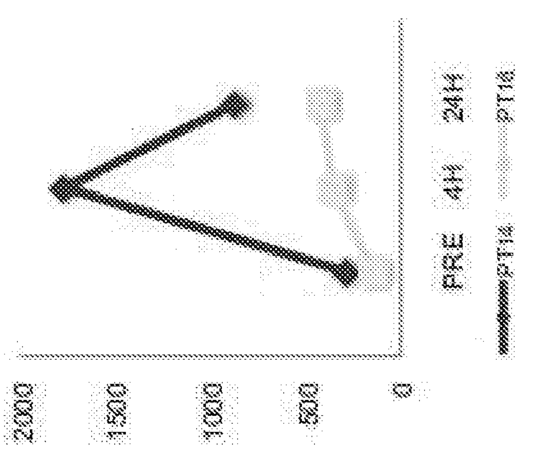

Kinetics of IFNβ (increase) and IFNα (decrease) indicate that day 2 would be suitable time point to measure IFNβ as a pharmacodynamics (PD) marker of Voyager-V1 infection in tumors. In particular, FIGS. 4A-4F show the comparison of relative IFNβ and IFNα trends in patients. FIGS. 4A-4C show that the IFNβ level (the dark line) increases at 24 hours post administration. FIGS. 4D-4F show that the IFNα level (the dark line) in the same patients decreases at 24 hours post administration. The data indicate that IFNβ transgene levels can serve as a PD marker of viral infection in tumors.

In conclusion, Voyager-V1 was given to 51 subjects by IT or IV routes. No viral shedding was observed in buccal swabs or urine. Plasma levels of IFNβ is a good early indicator of viral replication and may be a good PD marker for tumor susceptibility to Voyager-V1.

Example 3

Sub-Therapeutic Dose of IT Administration of Virus for Diagnostic Testing in Cancer Therapy There is a longstanding need for early assessment of an individual patient's response to cancer therapy and adapting the treatment decisions based on the individual response and changing circumstances in each patient. The understanding of an individual patient's tumor microenvironment and immune response to a cancer therapeutic agent can inform the choice of the most effective therapeutic regimen tailored for the specific individual.

Further, as shown above in Example 2, circulating levels of IFNβ is a good early indicator of viral replication and a good PD marker for tumor susceptibility to Voyager-V1. Thus, it is important to know the lowest dose of Voyager-V1 that can produce a detectable signal of IFNβ from an easily obtainable sample, such as blood, serum, or plasma.

Figures 5A, 5B, 5C, 5D, 5E, 5F:
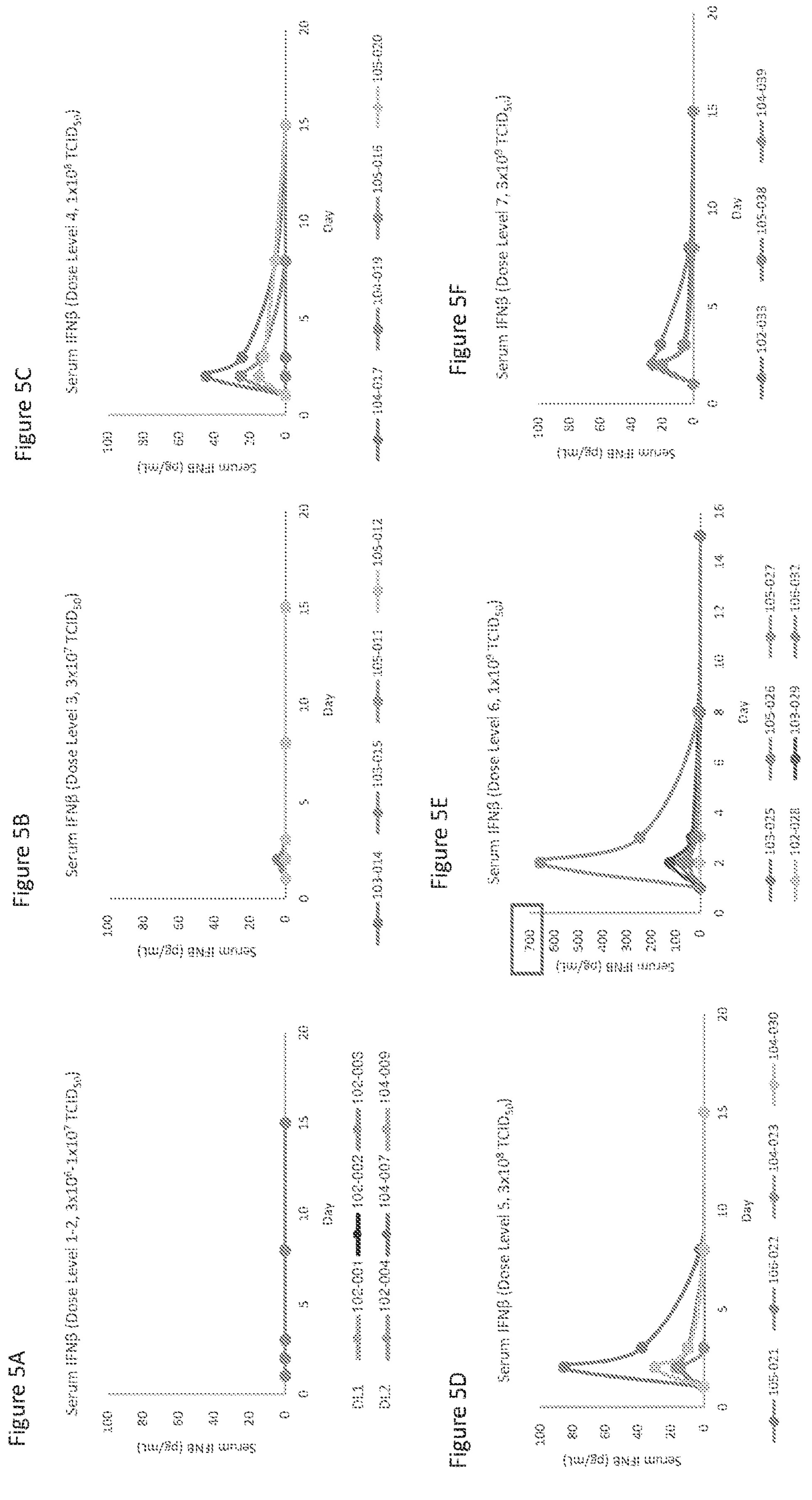
FIGS. 5A-5F show that the circulating levels of IFNβ detected in serum is an indicator of variability in Voyager-V1 infection and spread in individual patients. In particular.

Various doses of Voyager-V1 were given to patients with a variety of solid tumors intratumorally. The tested doses ranged from $3\times10^6$ to $3\times10^9$ TCID50. The circulating levels of IFNβ is serum can be detected even in patients given sub-therapeutic and non-toxic intratumoral doses as low as about $3\times10^7$ TCID50. See, for example, FIGS. 5A-5C. In addition, from DL4 onwards ($1\times10^8$ TCID50), both increased frequency in detectable circulating IFNβ levels and increase in the levels of circulating IFNβ with increase in dose levels were observed. See, for example, FIGS. 5B-5E. Thus, a low dose of Voyager-V1 that is not toxic and not therapeutic can be used to identify the likelihood that a cancerous tissue in a patient will respond to administration of a cancer therapy regimen.

In addition, this method can be used with not only Voyager-V1 but also any oncolytic virus probe, in particular, GMP grade virus, which comprises a nucleic acid encoding a soluble IFNβ. It was established in the Examples provided above that circulating IFNβ level can be a good indicator of variability in virus infection and spread in individual patients. In the case of Voyager-V1, the sub-therapeutic probing dose can be as low as approximately $10^6$ TCID50 to about $10^8$ TCID50, and it can be given intratumorally (as shown in FIGS. 5A-5F), or more conveniently, intravenously.

Example 4

Sample Collection and Preparation

Samples from patients can be collected using appropriate protocol available in the art. An exemplary sample collection procedure used by the study is provided herein.

Blood (1×1.5 mL) was drawn in one 5 mL red-top tube. Sample were collected at the following intervals: day 1 pre-treatment, days 2, 3, 4 (for IT+IV patients only), 8 and 15. Samples should only be drawn at day 22 and day 43 if day 15 is positive.

Samples were processed according to the following protocol. Invert tube gently 5 times. Allow the sample to rest for 30-60 minutes. Then spin down for 15 minutes at 2200-2500 RPM. Transfer 1-2 mL of serum (supernatant) into a 2 mL plastic cryovial. Samples should be transferred to a −80° C. freezer. Samples then were stored and transported to a facility for testing. When preparing the samples for shipment, it is critical to keep all samples fully frozen. Polystyrene containers with dry ice can be used for temporary storage/manipulation of samples outside the −80° C. freezer.

Example 5

Assay for IFNβ

The IFNβ levels from patient samples were evaluated by standard ELISA assay using the VeriKine-HS™ Human IFN Beta Serum ELISA Kit (Catalog No. 41415-1, PBL Assay Science, Piscataway Township, NJ) following the manufacturer's instruction provided in Protocol A (Enhanced protocol for improved performance in serum evaluation).

An exemplary protocol is provided as following. In each well, add the following sequentially: 50 μl sample buffer, 50 μl diluted antibody, and 50 μl test sample, IFN-β standard, or blank. Incubate for 2 hours while shaking at 450 rpm. Aspirate and wash 3 times. Add 100 μl diluted HRP solution. Incubate 30 minutes with shaking at 450 rpm. Aspirate and wash 4 times. Then add 100 μl TMB substrate. Incubate for 60 minutes in the dark. Do not seal, shake, or wash. Add 100 μl stop solution. Read plate within 5 minutes at 450 nm. All incubations are at room temperature (22° C. to 25° C.). The total assay time is about 3 hours 30 minutes.

The standard curve was prepared according to the following protocol: a) Label 8 polypropylene tubes (S1-S8). b) Add indicated volumes of Standard Diluent or sample matrix to the labeled tubes following the manufacture's instruction provided in Protocol A. c) Add 10 μl of IFN Standard to 90 μl of Standard Diluent or sample matrix using polypropylene tips. Set the volume to 80 μl and mix thoroughly by pipetting up and down 10 times using a 100 μl or 200 μl pipette. d) Add 7.5 μl of the 1:10 prediluted standard to S8 and mix thoroughly to recover all material adhered to the inside of the pipette tip. e) Using a pipette set at 250 μl, mix S8 thoroughly by pipetting up and down 10 times. Transfer 250 μl of S8 to S7 and mix thoroughly by pipetting up and down 5 times. Repeat to complete series to S1. f) Set aside until use in step 1 of the assay procedure.

Example 6

Treating Cancer Patients Who are Likely Responders to Viral Therapy

Following the administration of first therapeutic dose or a sub-therapeutic dose of Voyager-V1 in a subject diagnosed with cancer, circulating IFNβ levels can be detected from a sample obtained from the subject using the methods provided above.

Subjects having a plasma IFNβ level greater than about 1000 pg/mL have tumors that are highly susceptible to viral therapy. These subjects can be identified as strong responders and can be given additional therapeutic doses of Voyager-V1 or another oncolytic virus, for examples within a week. Subjects having a plasma IFNβ level between about 10 pg/mL to about 1000 pg/mL have tumor infected by virus immunologically at the measured time point. These subjects are identified as intermediate responders at this dose and should be given additional therapeutic doses of Voyager-V1, or another oncolytic virus, in combination with other cancer therapeutic agents. Subjects having a plasma IFNβ level lower than about 10 pg/mL have tumors not responsive to the viral therapy. These subjects can be identified as low responders and should be given other cancer therapeutic agents or booster drugs. The other cancer therapeutic agents can be, for example, immunotherapy, chemotherapy agents, radiation therapy, hormone therapy, etc. the immunotherapy can be immune checkpoint inhibitors, such as PD-L1 inhibitors.

The levels of circulating IFNβ P can be assessed at any time between 12 hours and 10 days post the administration of the first therapeutic dose or the sub-therapeutic dose of Voyager-V1. For example, the circulating IFNβ levels can be assessed at about 12 to 24 hours post administration, or at about 24-48 house post administration.

If circulating levels of IFNβ are too high, for example, greater than or equal to 10,000 pg/mL, within about 12-48 hours after the first administration of Voyager-V1, the patient will be given one or more therapeutic doses of a janus kinase inhibitor (JAK inhibitor). The JAK inhibitor can be, for example, ruxolitinib, or any JAK inhibitor that is commonly used.

What is claimed:

1. A method of determining the likelihood that a cancerous tissue in a subject having the cancerous tissue will respond to administration of an oncolytic virus cancer therapy regimen and treating said subject, the method comprising:

(a) administering intratumorally to the cancerous tissue from about $10^5$ tissue culture infectious dose 50 (TCID50) to about $3\times10^9$ TCID50 of a recombinant oncolytic virus probe that comprises a nucleic acid sequence that encodes a nucleocapsid (N) polypeptide, a nucleic acid sequence that encodes a phosphoprotein (P) polypeptide, a nucleic acid sequence that encodes a matrix (M) polypeptide, a nucleic acid sequence that encodes a glycoprotein (G) polypeptide, a nucleic acid sequence that encodes a viral polymerase (L) polypeptide, a nucleic acid that codes for soluble interferon beta (IFNβ), (b) measuring the circulating level of IFNβ in the subject after administration of the recombinant oncolytic virus probe to determine if the cancerous tissue will respond to the oncolytic virus cancer therapy regimen as (1) a strong responder, (2) an intermediate responder, or (3) a low responder or a non-responder, wherein a circulating IFNβ level in the subject greater than about 1000 pg/mL identifies the subject as the strong responder, a circulating IFNβ level in the subject between about 10 pg/mL to about 1000 pg/mL identifies the subject as the intermediate responder, and a circulating IFNβ level lower than about 10 pg/mL identifies the subject as the low responder or non-responder, and (c) administering the oncolytic virus cancer therapy regimen if the cancerous tissue is determined to be the strong responder, administering the oncolytic virus cancer therapy regimen and a cancer therapeutic agent other than the oncolytic virus cancer therapy regimen if the cancerous tissue is determined to be an intermediate responder, or administering a cancer therapeutic agent other than the oncolytic virus cancer therapy regimen if the cancerous tissue is determined to be a low responder or a non-responder.

2. The method of claim 1, where the oncolytic virus cancer therapy regimen comprises the recombinant oncolytic virus probe that is administered intratumorally in (a).

3. The method of claim 1, wherein the where the oncolytic virus cancer therapy regimen comprises a different recombinant oncolytic virus probe than what is administered intratumorally in (a).

4. The method of claim 1, wherein the oncolytic virus cancer therapy regimen comprises a cancer immunotherapy.

5. The method of claim 1, wherein the recombinant oncolytic virus probe is generated from a Good Manufacturing Practices (GMP) grade virus.

6. The method of claim 1, wherein the recombinant oncolytic virus probe is generated from a vesicular stomatitis virus (VSV).

7. The method of claim 1, wherein the recombinant oncolytic virus probe further comprises a nucleic acid encoding a sodium iodine symporter (NIS).

8. The method of claim 7, wherein the recombinant oncolytic virus probe has the construct of N-P-M-IFNβ-G-NIS-L.

9. The method of claim 1, wherein the circulating level of IFNβ are measured in the subject between about 12 hours to about 45 days after administration of the oncolytic virus.

10. The method of claim 1, wherein the circulating level of IFNβ is measured by an immunological assay.

11. The method of claim 1, wherein the cancerous tissue is a head and neck cancer, colon cancer, rectal cancer, pancreatic cancer, bladder cancer, breast cancer, hepatocellular cancer, lung cancer, medulloblastoma, atypical teratoid/rhabdoid tumor, a leukemia, a lymphoma, or a myeloma.

12. A method of treating cancer in a subject, comprising:

(a) identifying the likelihood that the cancerous tissue in a subject having the cancerous tissue will respond to administration of an oncolytic virus cancer therapy regimen, according to the method of claim 1, and (b) administering the oncolytic virus cancer therapy regimen if the cancerous tissue is determined to be a strong or intermediate responder.

13. The method of claim 12, wherein the oncolytic virus cancer therapy regimen comprises administration of a cancer immunotherapy.

14. The method of claim 12, wherein the cancerous tissue is a solid tumor and the oncolytic virus cancer therapy regimen is an oncolytic virus that is administered intratumorally.

15. The method of claim 12, wherein the oncolytic virus cancer therapy regimen is an oncolytic virus that is administered intravenously.

16. A method of treating cancer in a subject, comprising:

(a) identifying the likelihood that the cancerous tissue in a subject having the cancerous tissue will respond to administration of an oncolytic virus cancer therapy regimen, according to the method of claim 1, and (b) administering the oncolytic virus cancer therapy regimen and a cancer therapeutic agent other than the oncolytic virus cancer therapy regimen if the cancerous tissue is determined to be an intermediate responder.

17. The method of claim 16, wherein the cancer therapeutic agent is selected from the group consisting of an immunotherapy, a chemotherapy agent, radiation therapy, and hormone therapy.

18. A method of treating cancer in a subject, comprising:

(a) identifying the likelihood that the cancerous tissue in a subject having the cancerous tissue will respond to administration of an oncolytic virus cancer therapy regimen, according to the method of claim 1, and (b) administering a cancer therapeutic agent other than the oncolytic virus cancer therapy regimen if the cancerous tissue is determined to be a low responder or a non-responder.

19. The method of claim 18, wherein the cancer therapeutic agent is selected from the group consisting of an immunotherapy, a chemotherapy agent, radiation therapy, and hormone therapy.

* * * * *